United States Patent [19]

Hall et al.

[11] Patent Number: 4,548,821
[45] Date of Patent: Oct. 22, 1985

[54] FLAVORING WITH TERTIARY PENTAMETHYLINDANOL DERIVATIVES

[75] Inventors: John B. Hall, Rumson; Takao Yoshida, West Long Branch, both of N.J.

[73] Assignee: International Flavors & Fragrances Inc., New York, N.Y.

[21] Appl. No.: 702,361

[22] Filed: Feb. 15, 1985

Related U.S. Application Data

[62] Division of Ser. No. 589,662, Mar. 14, 1984, Pat. No. 4,520,032.

[51] Int. Cl.$^4$ .................. A23L 1/226; A23L 1/235
[52] U.S. Cl. .................................................... 426/3
[58] Field of Search ................. 426/538, 3; 568/819

[56] References Cited

U.S. PATENT DOCUMENTS

| | | | |
|---|---|---|---|
| 3,636,165 | 1/1972 | Hall | 568/819 |
| 3,647,826 | 3/1972 | Hall | 549/545 |
| 3,681,464 | 8/1972 | Theimer | 568/819 X |
| 3,703,479 | 11/1972 | Theimer | 568/819 X |
| 3,767,713 | 10/1973 | Theimer | 568/819 |
| 3,773,836 | 11/1973 | Hall | 568/819 X |
| 3,847,993 | 11/1974 | Hall | 568/819 X |
| 3,890,395 | 6/1975 | Jeger et al. | 568/819 |
| 3,911,027 | 10/1975 | Skorianetz | 568/819 |

*Primary Examiner*—Joseph Golian
*Attorney, Agent, or Firm*—Arthur L. Liberman

[57] ABSTRACT

Described are tertiary pentamethylindanol derivatives defined according to the structure:

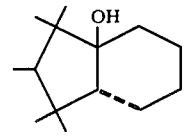

wherein the dashed line represents a carbon-carbon single bond or a carbon-carbon double bond and uses thereof in augmenting or enhancing the aroma or taste of consumable materials selected from the group consisting of perfume compositions, colognes, perfumed articles, foodstuffs, smoking tobaccos and smoking tobacco compositions.

3 Claims, 14 Drawing Figures

GLC PROFILE FOR EXAMPLE I
FRACTION 2.
1ST DISTILLATION

GLC PROFILE FOR EXAMPLE I.
CRUDE

GLC PROFILE FOR FRACTION 7 OF EXAMPLE I, SECOND DISTILLATION.

GS-MASS SPECTRUM FOR EXAMPLE I

FIG. 7 GLC PROFILE FOR FRACTION 5 OF EXAMPLE II.

FIG. 8 NMR SPECTRUM FOR FRACTION 5 OF EXAMPLE II.

GLC PROFILE FOR FRACTION 3 OF EXAMPLE III.

GLC PROFILE FOR FRACTION 1 OF EXAMPLE IV. REDISTILLATION.

GLC PROFILE FOR FRACTION 1 OF EXAMPLE IV. 1ST DISTILLATION

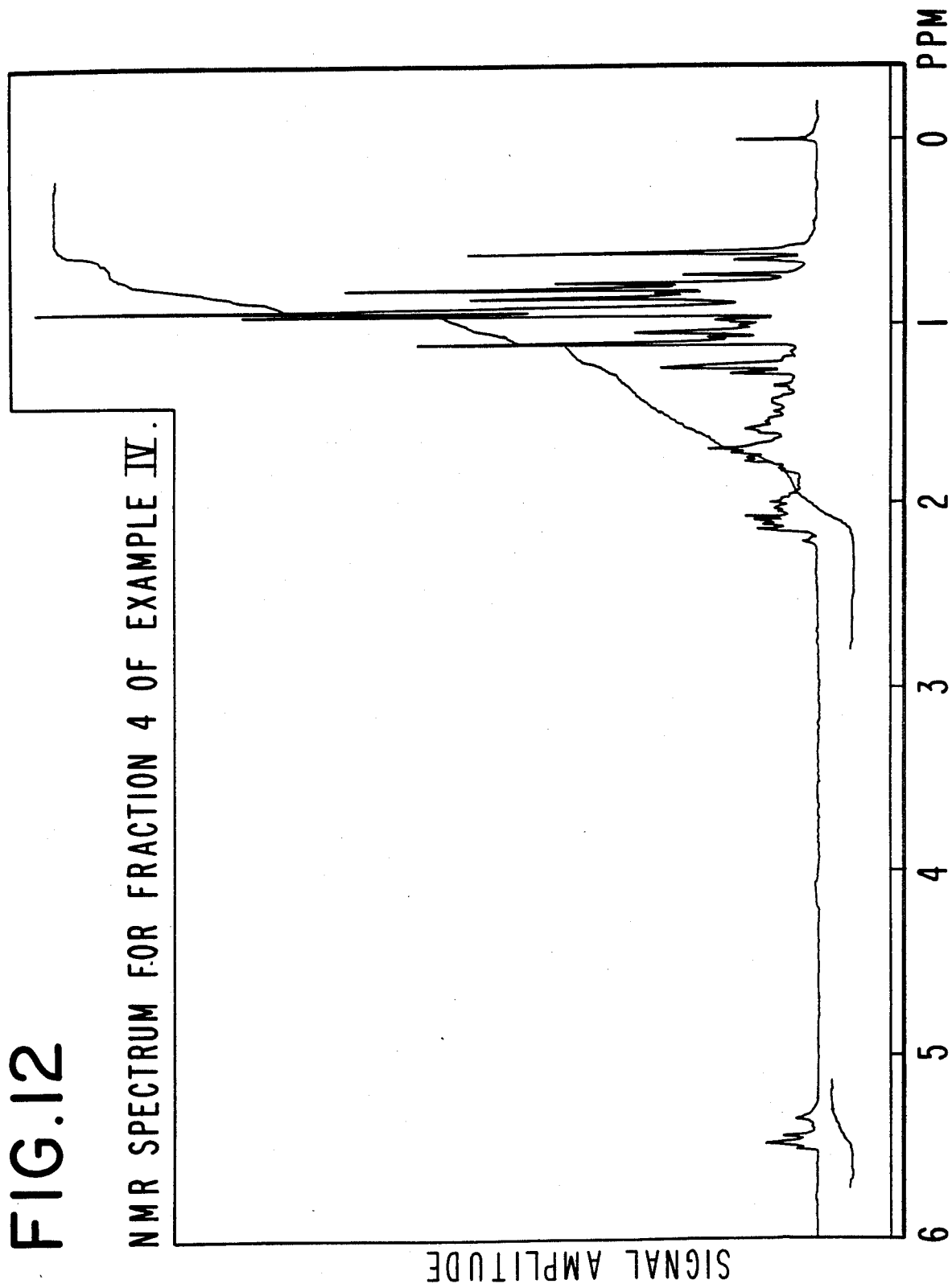
FIG. 12 NMR SPECTRUM FOR FRACTION 4 OF EXAMPLE IV.

FLAVORING WITH TERTIARY PENTAMETHYLINDANOL DERIVATIVES

This is a divisional of application Ser. No. 589,662 filed Mar. 14, 1984, now U.S. Pat. No. 4,520,032.

BACKGROUND OF THE INVENTION

The present invention relates to tertiary pentamethylindanol derivatives defined according to the structure:

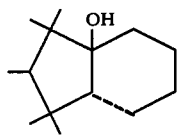

wherein the dashed line represents a carbon-carbon single bond or a carbon-carbon double bond and uses of such compounds in augmenting or enhancing the aroma or taste of perfume compositions, perfumed articles, colognes, foodstuffs, smoking tobacco compositions and smoking tobacco articles.

There has been considerable work performed relating to substances which can be used to impart (modify, augment or enhance) flavors and fragrances to (or in) various consumable materials. Such substances are used to diminish the use of expensive natural materials some of which may be in short supply and to provide more uniform properties in the finished product.

Leafy, patchouli-like, vetiver-like, ginseng-like, piney, rooty, woody and camphoraceous aromas with leafy, green, camphoraceous, woody, patchouli-like, musk, rooty, earthy and piney undertones are particularly desirable in several types of perfume compositions, perfumed articles and colognes.

Musky, patchouli-like and earthy aromas and musky tastes are useful in several types of foodstuffs, particularly walnut flavored foodstuffs and blackberry flavored foodstuffs.

Woody and oriental aroma and taste nuances are highly desirable in augmenting or enhancing the aromas and tastes of smoking tobacco both prior to and on smoking in the main stream and the side stream.

Pentamethylindanols are known to be useful in the fields of perfumery. Thus, U.S. Pat. No. 3,636,165 discloses the compound defined according to the structure:

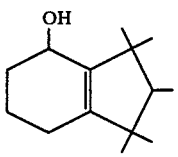

as being useful in augmenting or enhancing the aroma of perfume compositions and perfumed articles. This compound is disclosed in U.S. Pat. No. 3,636,165 to be produced from epoxy pentamethylindane according to the reaction:

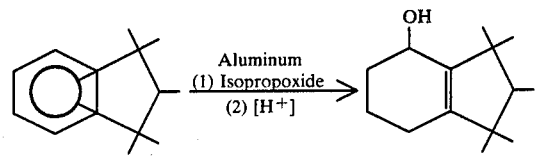

whereby the compound having the structure:

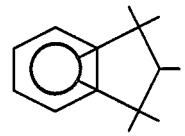

is reacted with aluminum isopropoxide and the workup is carried out under acidic conditions.

Nothing in the prior art however, discloses the preparation of tertiary pentamethylindanol derivatives which have unexpected, unobvious and advantageous organoleptic characteristics when compared to the chemicals of the prior art.

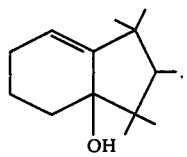

Figure 2:
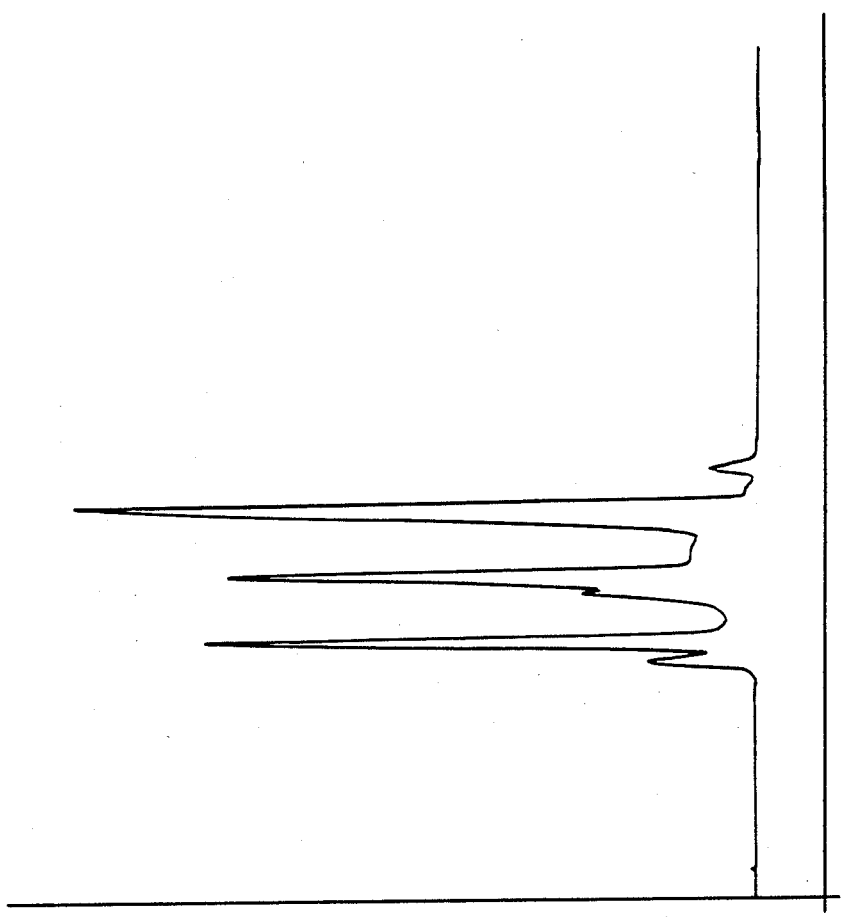

FIG. 2 is the GLC profile for Fraction 2 of the first distillation of the reaction product of Example I containing the compound having the structure:

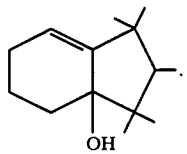

Figure 3:
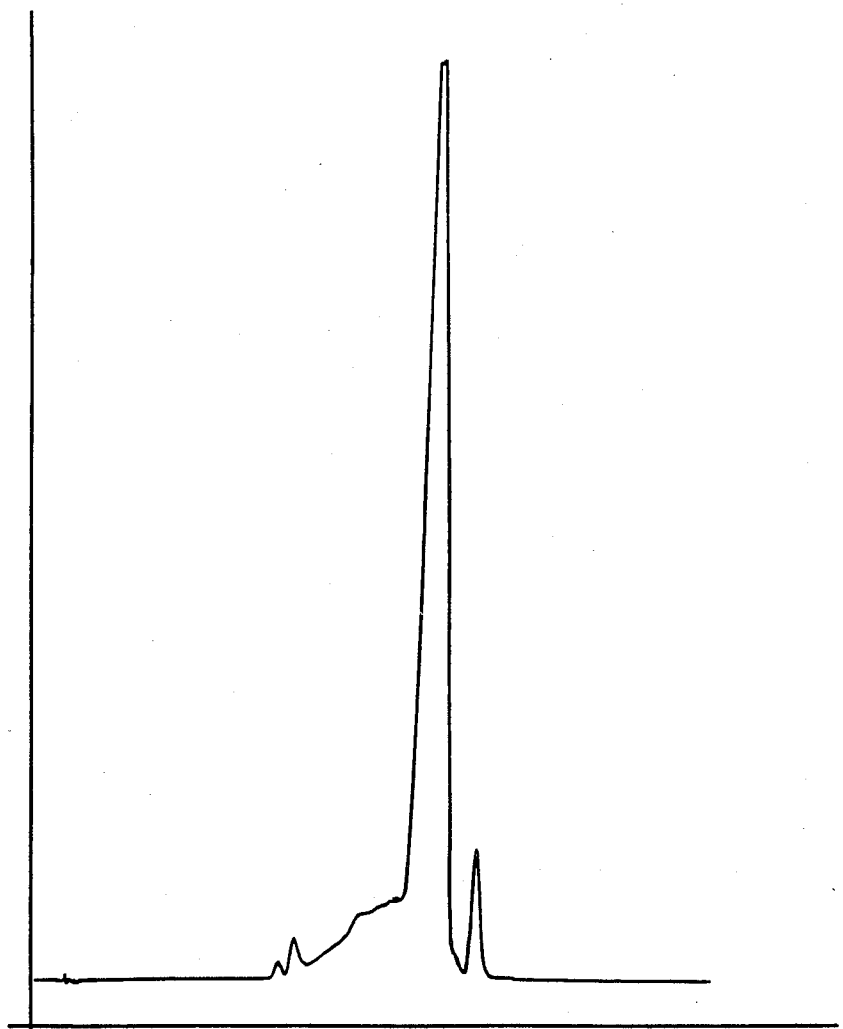

FIG. 3 is the GLC profile for Fraction 7 of the second distillation of the reaction product of Example I containing the compound having the structure:

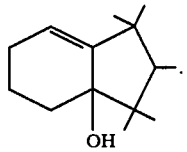

Figure 4:
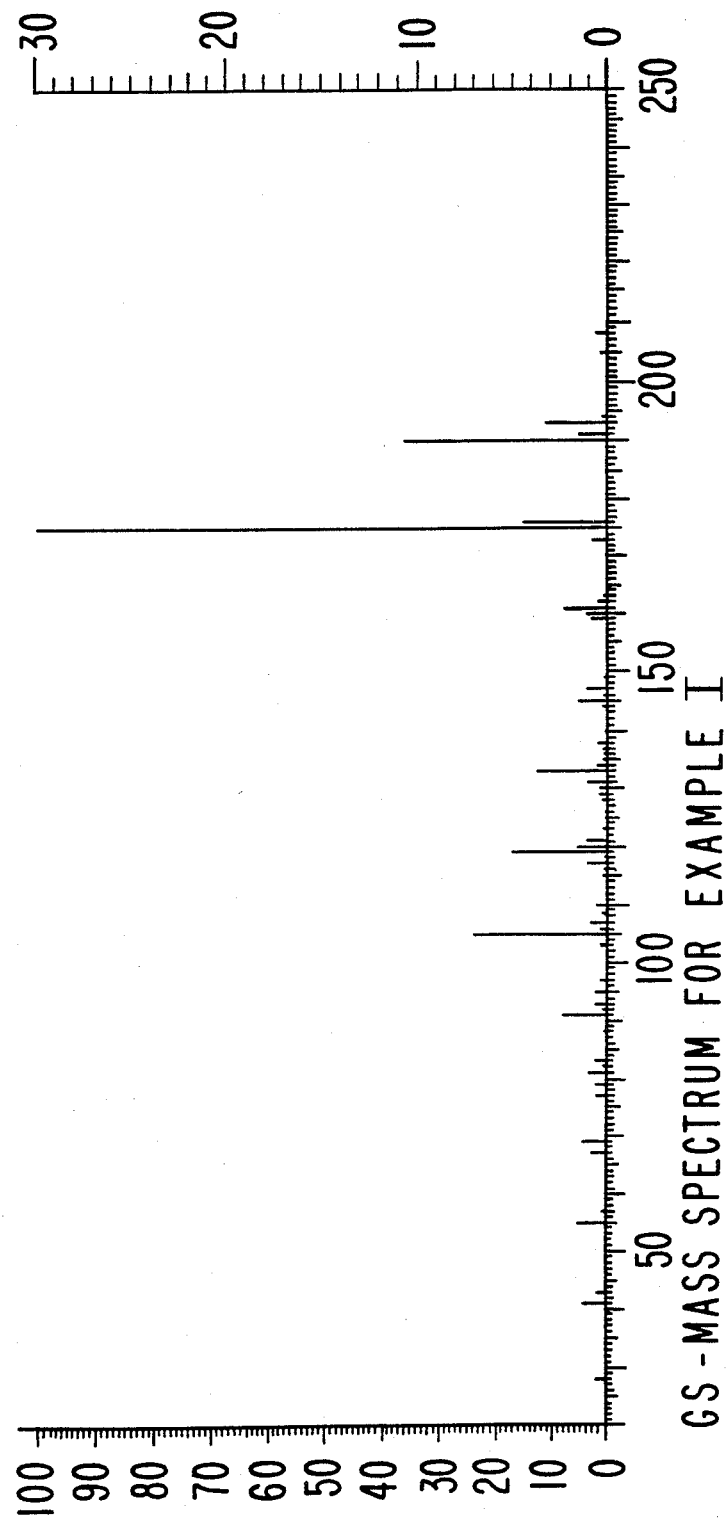

FIG. 4 is the GC-MS profile for the compound having the structure:

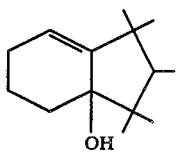

produced according to Example I.

Figure 5:
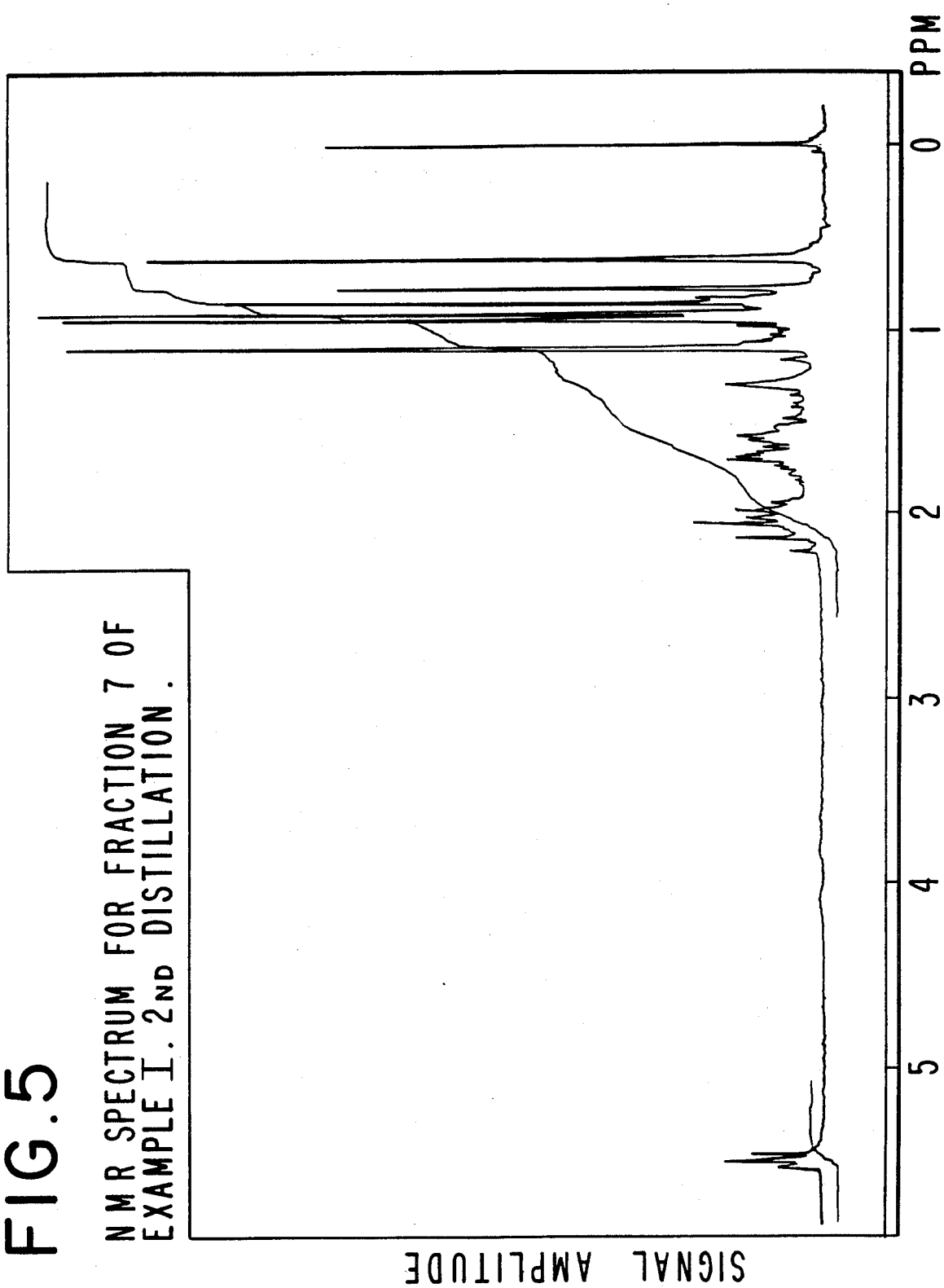

FIG. 5 is the NMR spectrum for Fraction 7 of the distillation of the reaction product of Example I containing the compound having the structure:

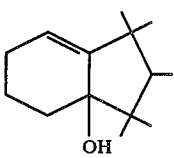

(conditions: Field strength: 100 MHz; Solvent: CFCl₃).

Figure 6:
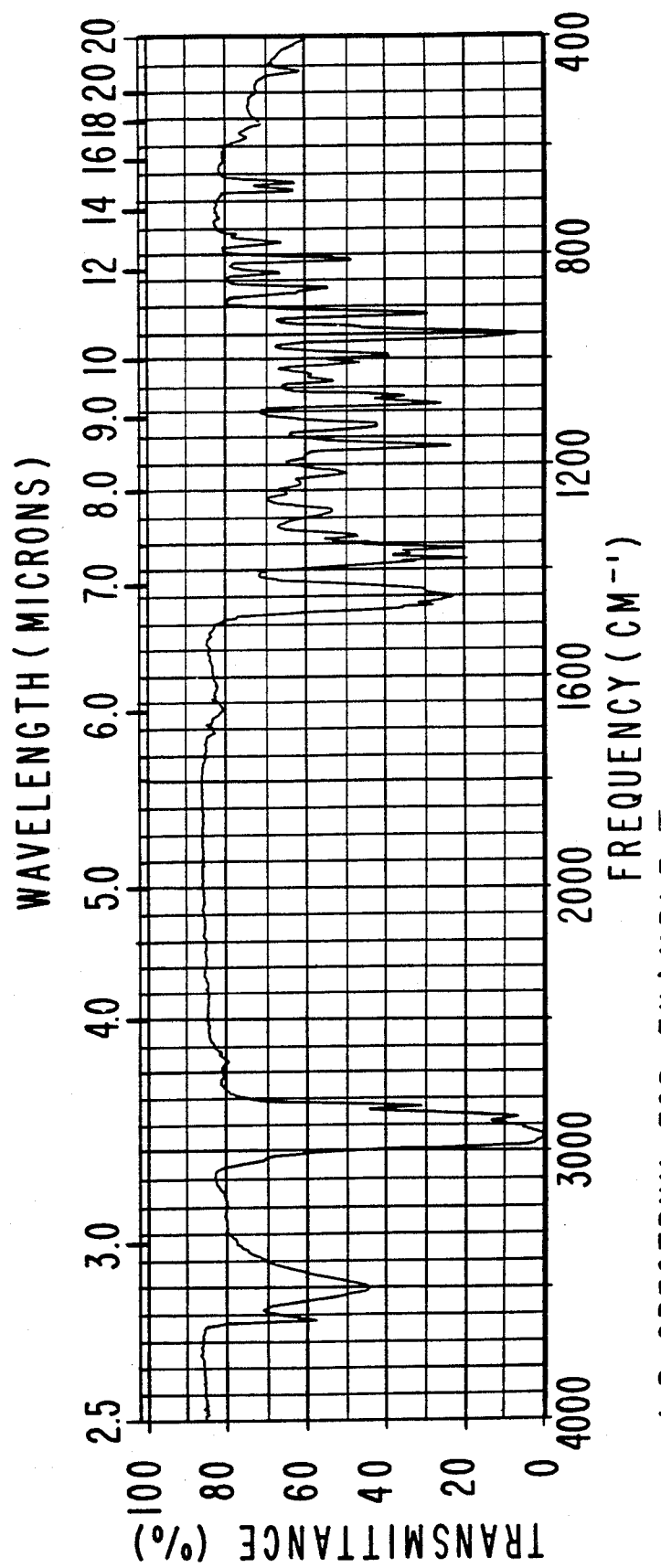

FIG. 6 is the Infra-red spectrum for the compound having the structure:

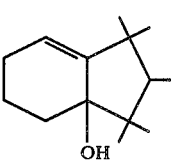

produced according to Example I.

Figure 7:
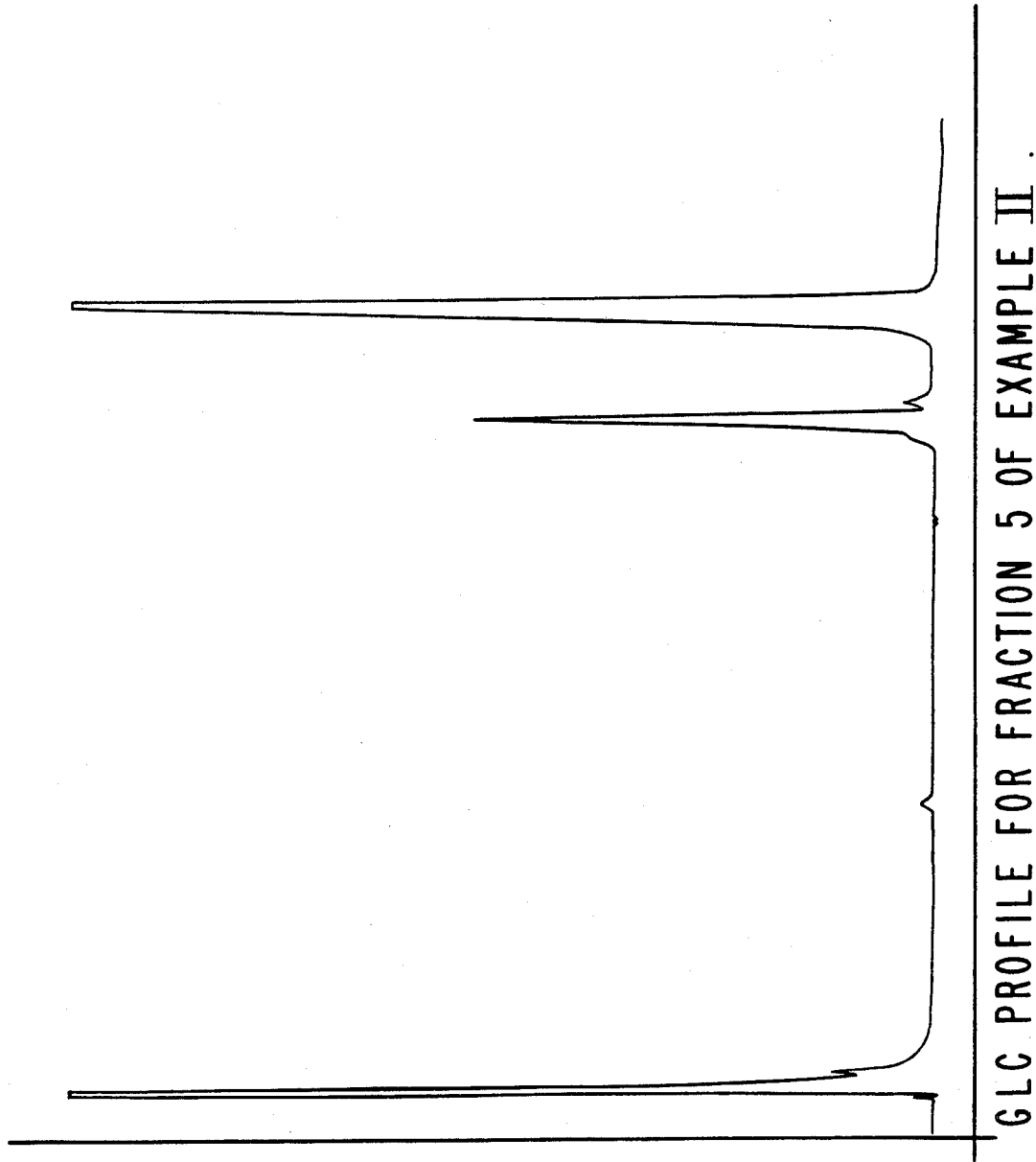

FIG. 7 is the GLC profile for Fraction 5 of the distillation of the reaction product of Example II containing the compound having the structure:

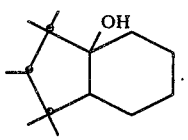

Figure 8:
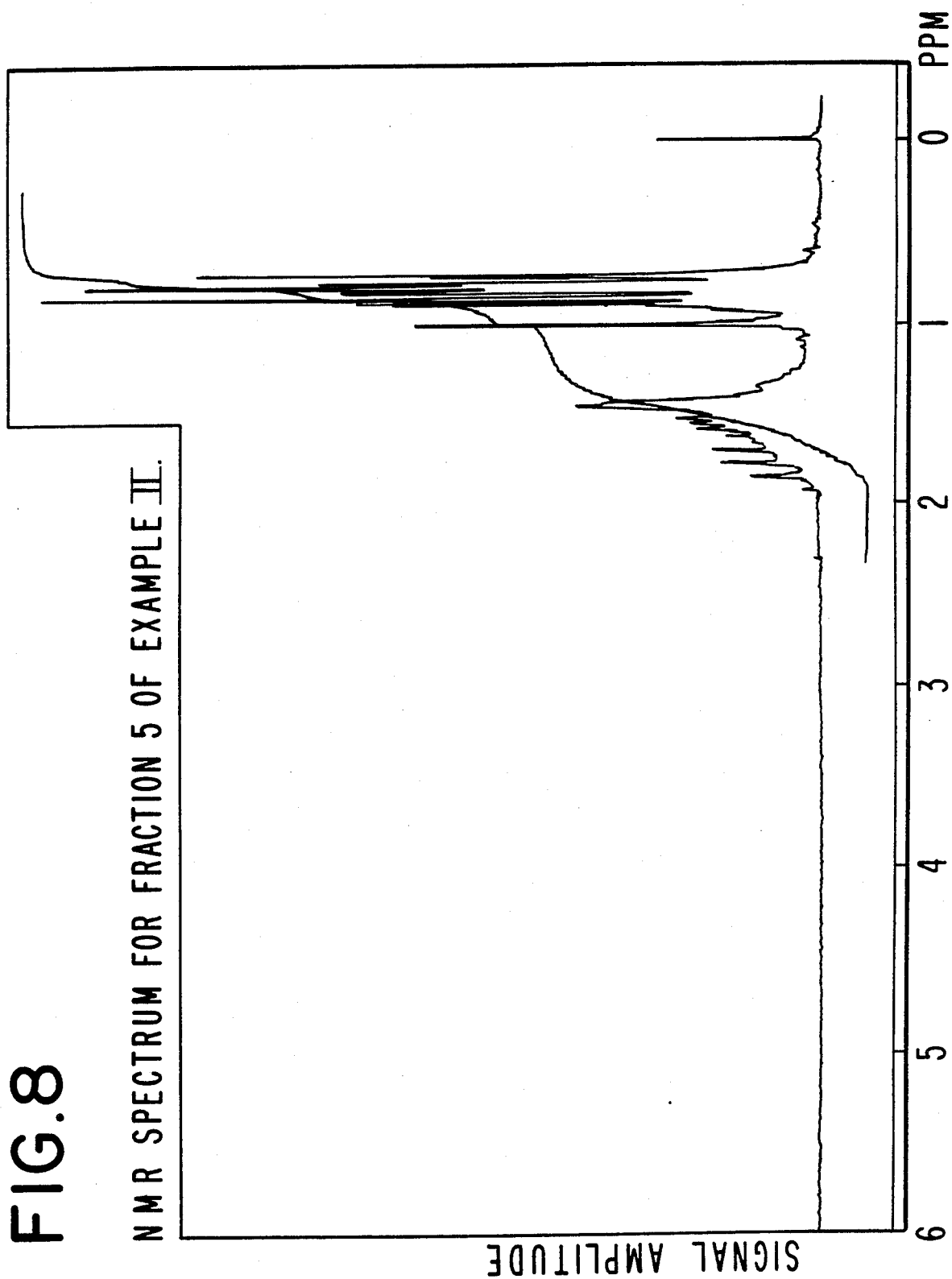

FIG. 8 is the NMR spectrum for Fraction 5 of the distillation of the reaction product of Example II containing the compound having the structure:

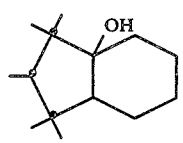

(conditions: Field strength: 100 MHz; Solvent: CFCl₃).

Figure 9:
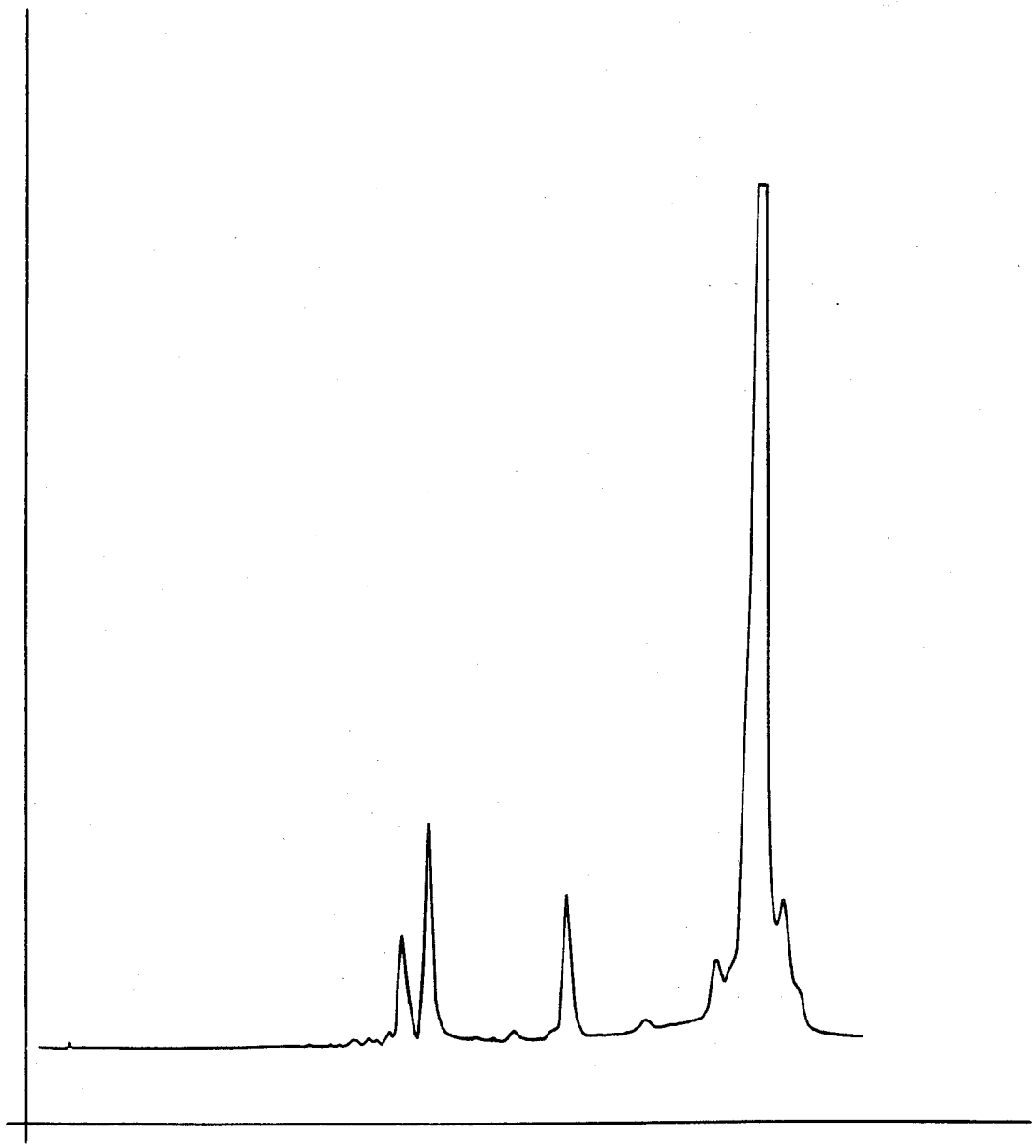

FIG. 9 is the GLC profile for Fraction 3 of the distillation of the reaction product of Example III containing the compound having the structure:

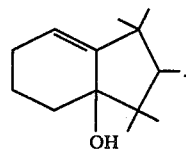

Figure 10:
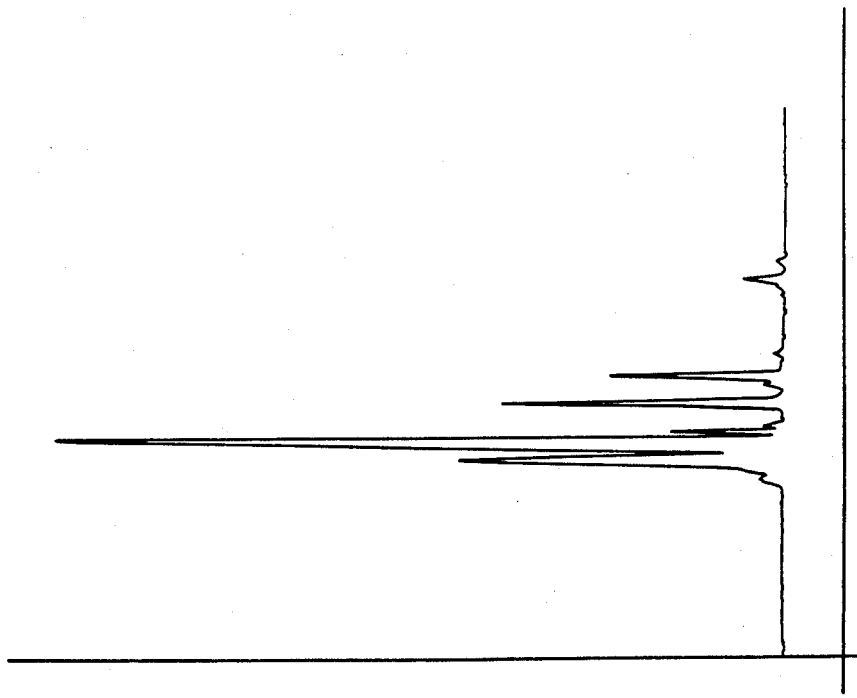

FIG. 10 is the GLC profile for Fraction 4 of the first distillation of the reaction product of Example IV containing the compound having the structure:

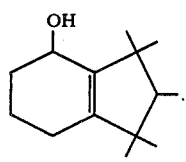

Figure 11:
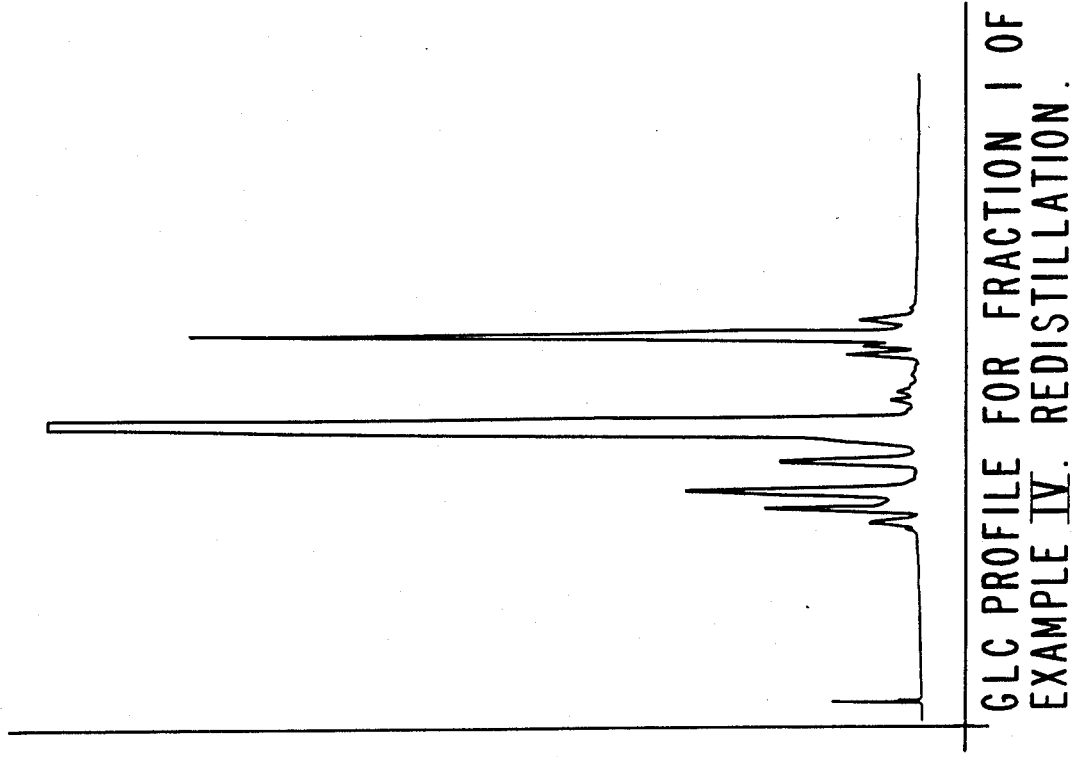

FIG. 11 is the GLC profile for Fraction 4 of the second distillation of the reaction product of Example IV containing the compound having the structure:

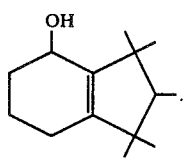

FIG. 12 is the NMR spectrum for Fraction 4 of the distillation of the reaction product of Example IV containing the compound having the structure:

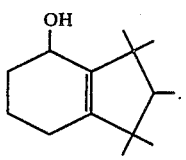

Figures 13, 14:
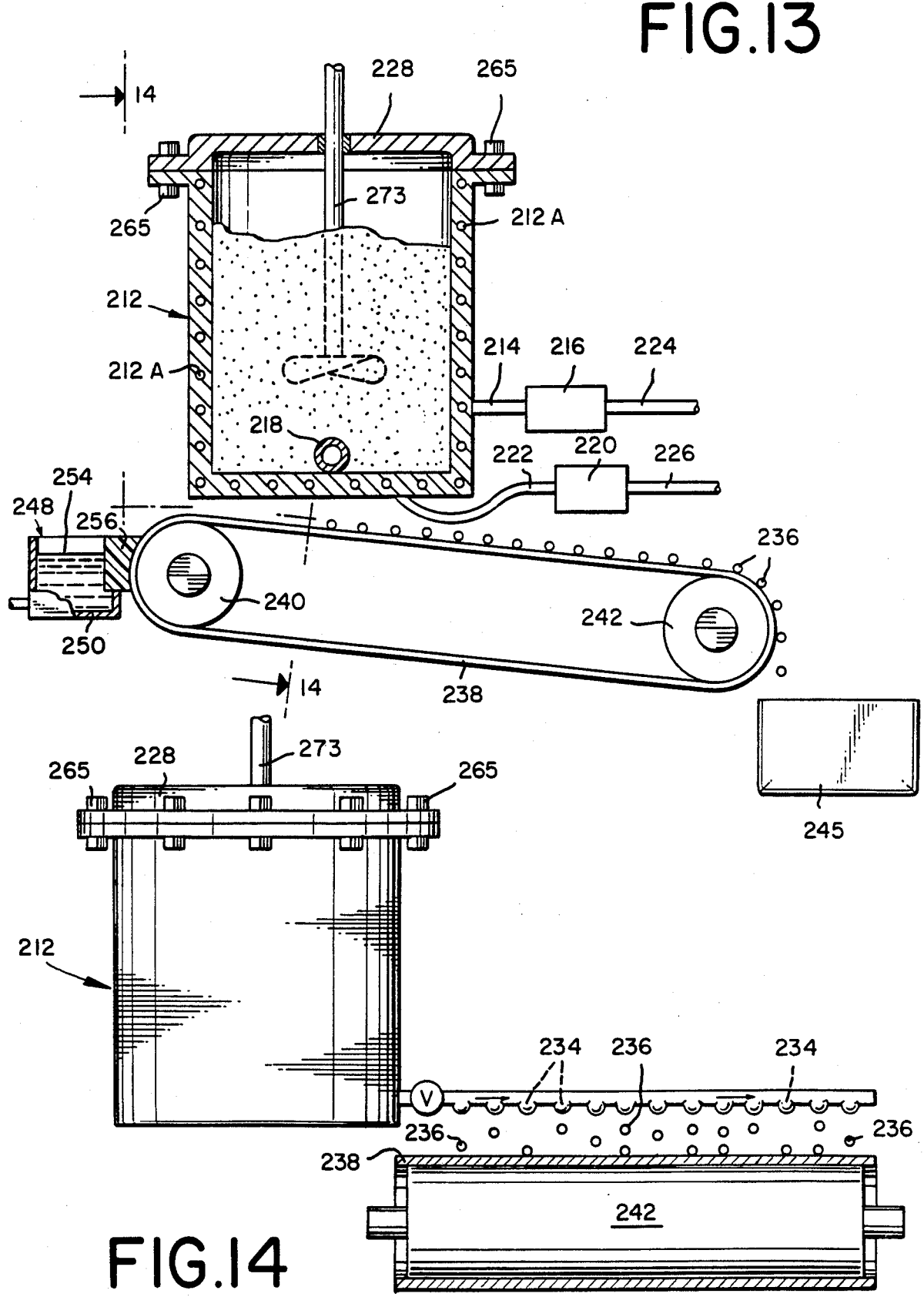

FIG. 13 represents a cut-away side elevation view of apparatus used in forming perfumed polymers which contain imbedded therein at least one of the tertiary pentamethylindanol derivatives of our invention.

FIG. 14 is a front view of the apparatus of FIG. 13 looking in the direction of the arrows.

DETAILED DESCRIPTION OF THE DRAWINGS

Referring to FIGS. 13 and 14, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS.

13 and 14, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the tertiary pentamethylindanol derivatives of our invention or mixtures of the tertiary pentamethylindanol derivatives and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within the temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the tertiary pentamethylindanol derivatives of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the tertiary pentamethylindanol derivatives of our invention or mixture of tertiary pentamethylindanol derivatives and one or more other substances, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the tertiary pentamethylindanol derivatives of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden amost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides tertiary pentamethylindanol derivatives defined according to the generic structure:

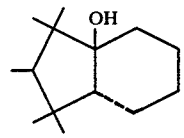

wherein the dashed line represents a carbon-carbon single bond or a carbon-carbon double bond.

The tertiary pentamethylindanol derivatives of our invention produced according to the processes of our invention are capable of augmenting or enhancing musky, patchouli-like and earthy aromas with musky taste characteristics of foodstuffs, foodstuff flavors, chewing gums, chewing gum flavors, medicinal products, medicinal product flavors, toothpastes and toothpaste flavors.

The tertiary pentamethylindanol derivatives of our invention as well as mixtures thereof are also capable of modifying or enhancing the aroma characteristics of perfume compositions, colognes and perfumed articles (including soaps, nonionic, anionic, cationic and zwitterionic detergents, fabric softener articles and perfumed polymers) by imparting thereto leafy, patchouli-like, vetiver-like, ginseng-like, piney, rooty, woody and camphoraceous aromas with leafy, green, camphoraceous, woody, patchouli-like, musk, rooty, earthy and piney undertones, thus fulfilling a need the field of perfumery.

In tobacco, tobacco flavoring, substitute tobacco and substitute tobacco flavoring compositions, the tertiary pentamethylindanol derivatives of our invention produced according to the process of our invention augment or enhance or impart woody, oriental-like and Turkish tobacco-like aroma and taste nuances to smoking tobacco and substitute smoking tobaccos prior to and on smoking in both the main stream and the side stream.

The tertiary pentamethylindanol derivatives of our invention are produced using as a starting material the epoxide derivative defined according to the structure:

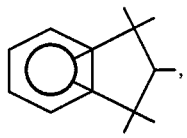

which, in turn, is produced according to the procedure of U.S. Pat. No. 3,647,826 issued on Mar. 7, 1972 the disclosure of which is incorporated by reference herein. The generic reaction to produce the compound defined according to the structure:

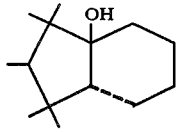

is shown thusly:

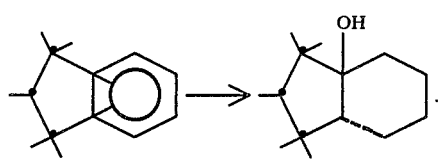

When producing the compound defined according to the structure:

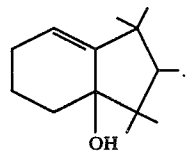

an aluminum alkoxide catalyst defined according to the structure:

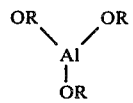

wherein R represents $C_3$ or $C_4$ alkyl is used followed by a workup using base (as opposed to acid, at a pH of less than 7). This reaction is shown thusly:

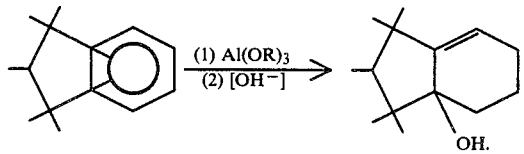

When using an acidic workup, the secondary alcohol defined according to the structure:

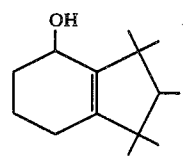

is formed rather than the tertiary alcohol having the structure:

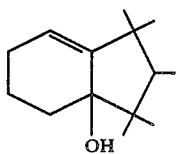

and, thus, the secondary alcohol having the structure:

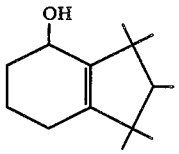

is formed according to the reaction:

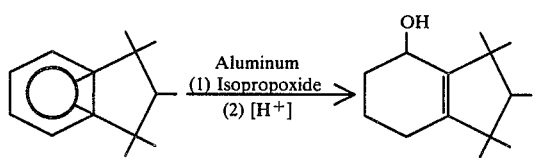

as per the teachings of U.S. Pat. No. 3,636,165 issued on Jan. 18, 1972, the specification for which is incorporated by reference herein.

In carrying out the reaction:

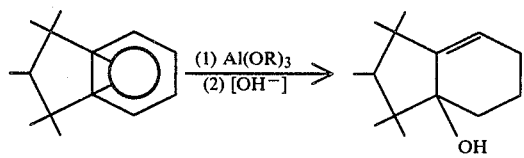

wherein R represents $C_3$–$C_4$ alkyl, the reaction is carried out at reflux conditions at a temperature in the range of from about 90° C. up to about 130° C. in the presence of an inert non-reactive solvent, that is, non-reactive to the epoxide product having the structure:

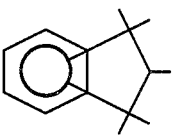

or the tertiary pentamethylindanol derivative having the structure:

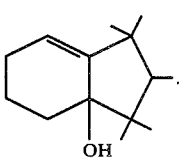

Typical solvents are toluene and xylene. The reaction pressure may vary from 0.8 atmospheres up to about 2 atmospheres with a pressure of 1 atmosphere being most convenient. The reaction time may vary from about one hour up to about thirty hours, greater reaction times giving rise to greater yields.

At the end of the reaction, the reaction mass is admixed with water and aqueous base at a pH of between about 9 and 11. The resulting reaction mass is then washed with water and the organic phase is then distilled, preferably by means of fractional distillation. Fractions of the resulting distillate are then selected for their organoleptic properties.

The tertiary pentamethylindanol derivative defined according to the structure:

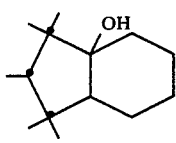

may be prepared from the epoxide having the structure:

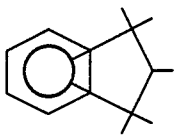

by means of reaction with lithium aluminum hydride or reaction with a mixture of lithium and ethylene diamine according to one of the reactions:

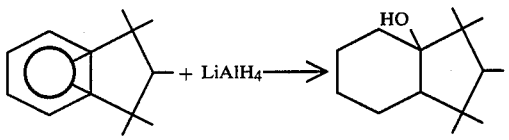

or

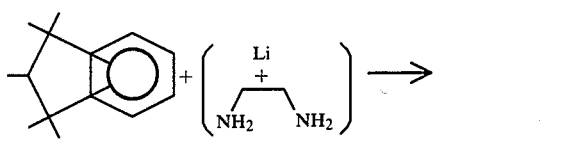

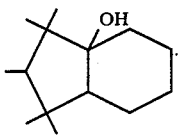

The reaction with lithium aluminum hydride and the compound having the structure:

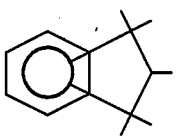

is carried out under reflux conditions at a temperature in the range of from about 160° C. up to about 200° C. at atmospheric pressure. The time of reaction may vary from about two hours up to about thirty hours with the optimum reaction time being in the range of from about nine hours up to about twelve hours when carrying out the reaction at reflux at a temperature of between 170° C. and 180° C. The reaction is carried out in the presence of a solvent suitable to maintain the above-mentioned reaction conditions, e.g., diglime which will cause the reaction to be carried out at about 170°–180° C. at one atmosphere pressure. The mole ratio of lithium aluminum hydride: to epoxide having the structure:

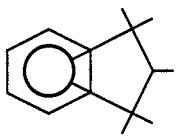

is about 1:1. At the end of the reaction, the reaction mass is quenched with water and base such as aqueous dilute sodium hydroxide. The organic layer is then separated and distilled and the resulting fractions are bulked and utilized for their organoleptic properties.

When carrying the reaction of the compound having the structure:

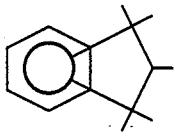

with lithium and ethylene diamine, according to the reaction:

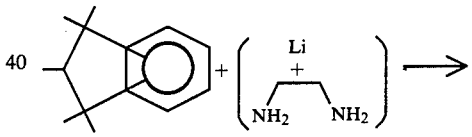

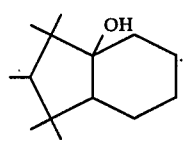

the reaction is carried out at a temperature of between 45° and 60° C. at atmospheric pressure for a period of time of between about one and about three hours. An excess of ethylene diamine is used and, accordingly, the mole ratio of ethylene diamine:epoxide defined according to the structure:

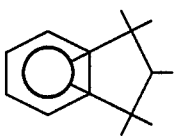

may vary from about 2:1 up to about 5:1. The mole ratio of lithium metal:ethylene diamine may vary from about 0.9:1 up to about 1:0.9 with the ethylene diamine being preferred to be in molar excess. At the end of the reaction, the reaction mass is quenched with water and extracted with a solvent such as diethyl ether. The extract is stripped of solvent and distilled preferably by means of fractional distillation. The resulting fractions are bulked and utilized for their organoleptic properties.

The following table sets forth the reaction products of our invention and their corresponding organoleptic properties:

may be plasticizers or softening agents, e.g., glycerine; and a flavoring composition which incorporates the tertiary pentamethylindanol derivatives of our invention and, in addition, sweetening agents which may be sugars, including sucrose or dextrose and/or artificial sweeteners such as cyclamates or saccharine. Other optional ingredients may also be present.

Substances for use herein as co-ingredients or flavor-

TABLE I

| Structure of Reaction Product | Perfume Properties | Food Flavor Properties | Tobacco Flavor Properties |
|---|---|---|---|
| The compound having the structure: 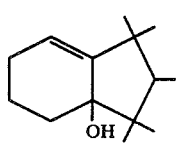 | A leafy patchouli-like, vetiver-like, and ginseng-like aroma with leafy, green, camphoraceous, woody, patchouli-like and musk undertones. | A musky, patchouli-like and earthy aroma with a musky taste at 1.0 ppm causing it to be useful in walnut and blackberry flavors. | A woody, oriental aroma and taste both prior to and on smoking in the main stream and the side stream. |
| The compound having the structure: 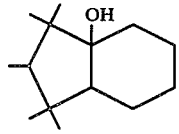 | A patchouli-like, piney, rooty, woody, camphoraceous aroma with rooty, earthy, camphoraceous, woody and piney undertones. | A patchouli-like aroma and taste profile at 5.0 ppm causing it to be useful in walnut flavors. | An oriental, Turkish tobacco aroma and taste profile both prior to and on smoking in the main stream and the side stream. |

When the tertiary pentamethylindanol derivatives produced according to the process of our invention are used as food flavor adjuvants, the nature of the co-ingredients included with the tertiary pentamethylindanol derivatives used in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soaps, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble chewable plastic gum base such as chicle, or substitutes therefor, including jelutong, guttakay rubber or certain comesible natural or synthetic resins or waxes. Incorporated with the gum base in admixture therewith ing adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may, in general, be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids, carbohydrates; starches, pectins and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, tumeric and curcuma and the like; firming agents such as aluminum sodium sulfate, calcoum chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, gerrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, cortonal, diacetyl, 2-methyl butanal, $\beta,\beta$-dimethyl acrolein, methyl-n-amyl ketone, n-hexanal, 2-hexenal, isopentanal, hydrocinnanic aldehyde, cis-3-hexenal, 2-heptenal nonyl aldehyde, 4-(p-hydroxyphenyl)-2-butanone, alpha-ionone, beta-ionone, methyl-3-butanone, benzaldehyde, $\beta$-damascone, $\beta$-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, n-hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines, such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as $\delta$-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the tertiary pentamethylindanol derivative(s) of our invention by not covering or spoiling the organoleptic properties (aroma and/or taste) thereof; (ii) be non-reactive with one or more of the tertiary pentamethylindanol derivatives of our invention and (iii) be capable of providing an environment in which the tertiary pentamethylindanol derivative(s) of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste or chewing tobacco to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of tertiary pentamethylindanol derivatives thereof of our invention employed in a particular instance can vary over a relatively wide range, depending upon the desired organoleptic effects to be achieved. Thus, correspondingly greater amounts would be necessary in those instances wherein the ultimate food composition to be flavored (e.g., a "raisin-rum cake") is relatively bland to the taste, whereas relatively minor quantities may suffice for purposes of enhancing the composition merely deficient in natural flavor or aroma, (e.g., when actual raisins and rum are present in the foodstuff such as the cake). The primary requirement is that the amount selected by effective, i.e., sufficient to alter, modify or enhance the organoleptic characteristics of the parent composition, whether foodstuff per se, chewing gum per se, medicinal product per se, toothpaste per se, chewing tobacco per se or flavoring composition.

The use of insufficient quantities of one or more tertiary pentamethylindanol derivatives of our invention will, of course, substantially vitiate any possibility of obtaining the desired results while excess quantities prove needlessly costly and in extreme cases, may disrupt the flavoraroma balance, thus proving self-defeating. Accordingly, the terminology "effective amount" and "sufficient amount" is to be accorded a significance in the content of the present invention consistent with the obtention of desired flavoring effects.

Thus, and with respect to ultimate food compositions, chewing gum compositions, medicinal product compositions, chewing tobacco compositions and toothpaste compositions, it is found that quantities of one or more tertiary pentamethylindanol derivatives of our invention ranging from a small but effective amount, e.g., about 0.05 parts per million up to about 150 parts per million based on total food composition or chewing gum composition, or medicinal product composition or tobacco composition or chewing tobacco composition are suitable. Concentrations in excess of the maximum quantity stated are not normally recommended since they fail to provide commensurate enhancement of organoleptic properties. In those instances where one or more tertiary pentamethylindanol derivatives of our invention are added to the foodstuff as an integral component of a flavoring composition, it is, of course, essential that the total quantity of flavoring composition employed be sufficient to yield an effective concentration of one or more tertiary pentamethylindanol derivatives of our invention in the foodstuff product.

Food flavoring compositions containing one or more of the compounds prepared in accordance with the present invention preferably contain one or more tertiary pentamethylindanol derivatives in concentrations ranging from about 0.02% up to about 15% by weight of the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or more of the tertiary pentamethylindanol derivatives of our invention prepared in accordance with our invention with, for example, gum arabic, gum tragacanth, xanthan gum, carrageenan and the like, and thereafter spray-drying the resultant mixture whereby to obtain the particulate solid product. Pre-prepared flavor mixes in powder form, e.g., a fruit flavored or rum flavored powder mix are obtained by mixing the dried solid components, e.g., starch, sugar and the like and one or more tertiary pentamethylindanol derivatives of our invention in a dry blender until the requisite degree of uniformity is achieved.

It is presently preferred to combine one or more tertiary pentamethylindanol derivatives of our invention with at least one of the following adjuvants:

p-Hydroxybenzyl acetone;
Genaniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl Acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethol;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,6,6-trimethylcyclohex-1-ene);
β-Damascenone (1-crotonyl-2,6,6-trimethylcyclohexa-1,3-diene);
Beta-cyclohomocitral (2,6,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene);
2-(4-Hydroxy-4-methylpentyl)norbornadiene rum essence
3-hydroxy butyric acid;
2-hydroxy butyric acid;
N-methyl anthranilate cyclotene;
ethyl cyclotene;
n-propyl cyclotene; and
gin berry essence.

One of the tertiary pentamethylindanol derivatives prepared in accordance with the process of our invention and one or more auxiliary perfume ingredients including, for examples, alcohols other than the tertiary pentamethylindanol derivatives of our invention, aldehydes, ketones, terpenic hydrocarbons, nitriles, esters, lactones, natural essential oils and synthetic essential oils may be admixed so that the combined odors of the individual components produce a pleasant and desired fragrance, particularly, and preferably, in piney fragrances and patchouli fragrances. Such perfume compositions usually contain (a) the main note or the "bouquet" or foundation stone of the composition; (b) modifieres which round off and accompany the main note; (c) fixatives which include odorous substances which lend a particular note to the perfume throughout all states of evaporation and substances which retard evaporation; and (d) topnotes which are usually low-boiling fresh-smelling materials.

In perfume compositions, it is the individual components which contribute to their particular olfactory characteristics, however, the overall sensory effect of the perfume composition will be at least the sum total of the effects of each of the ingredients. Thus, one of the tertiary pentamethylindanol derivatives prepared in accordance with the processes of our invention can be used to alter, modify, or enhance the aroma characteristics of a perfume composition, for example, by utilizing or moderating the olfactory reaction contributed by another ingredient in the composition.

The amount of one of the tertiary pentamethylindanol derivatives prepared in accordance with the processes of our invention which will be effective in perfume compositions as well as in perfumed articles (e.g., anionic, nonionic, cationic, or zwitterionic detergents, soaps and fabric softener compositions and articles) and colognes depends upon many factors including the other ingredients, their amounts of the effects which are desired. It has been found that perfume compositions containing as little as 0.01% of one of the tertiary pentamethylindanol derivatives prepared in accordance with the processes of our invention and less 50% of one of the tertiary pentamethylindanol derivatives prepared in accordance with the processes of our invention or even less (e.g., 0.005%) can be used to impart a leafy, patchouli-like, vertiver-like, ginseng-like, piney, rooty, woody, camphoraceous aroma with leafy, green, camphoraceous, woody, patchouli-like, musk, rooty, earthy and piney undertones to soaps, cosmetics, anionic, cationic, nonionic, or zwitterionic detergents, fabric softener compositions, fabric softener articles, perfumed polymers or other amounts. The amount employed can range up to 70% of the fragrance components and will depend on considerations of cost, nature of the end product, the effect desired on the finished product and the particular fragrance sought.

One or more of the tertiary pentamethylindanol derivatives prepared in accordance with the processes of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and such screens; powders, such as talcs, dusting powders, face powders, perfumed polymers and the like. When used as (an) olfactory component(s) as little as 0.2% of one or both of the tertiary pentamethylindanol derivatives of our invention, prepared in accordance with the process of our invention, will suffice to impart an intense leafy, patchouli-like, vetiver-like, ginseng-like, piney, rooty, woody, camphoraceous aroma with leafy, green, camphoraceous, woody, patchouli-like, musk, rooty, earthy and piney undertones to patchouli formulations and to vertiver formulations and to pine formulations. Generally, no more than 6% of one or both of the tertiary pentamethylindanol derivatives of our invention produced in accordance with the processes of our invention based on the ultimate end product are required in the perfumed article composition. Accordingly, the range of one or more of the tertiary pentamethylindanol derivates of our invention in a perfumed article may vary from about 0.2% up to about 6% by weight of the ultimate perfumed article.

In addition, the perfume compositions or fragrance compositions of our invention can contain a vehicle or carrier for one or both of the tertiary pentamethylindanol derivatives prepared in accordance with the processes of our invention. The vehicle can be a liquid, such as a non-toxic alcohol, e.g., ethyl alcohol, a glycol, e.g., propylene glycol or the like. The carrier can also be an absorbent solid, such as a gum (e.g., gum arabic, xanthan or guar gum) or components for encapsulating the composition (such as gelatin as by coacervation or such as urea-formaldehyde pre-polymer when forming a urea-formaldehyde polymer wall around a liquid perfume center).

It will thus be apparent that one or both of the tertiary pentamethylindanol derivatives of our invention produced in accordance with the processes of our invention can be utilized to alter, modify or enhance sensory properties, particularly organoleptic properties such as flavors and/or fragrances of a wide variety of consumable materials.

Furthermore, one or both of the tertiary pentamethylindanol derivatives of our invention prepared in accordance with the processes of our invention are capable of supplying and/or potentiating certain flavor and aroma notes usually lacking in many smoking tobacco flavors and substitute tobacco flavors provided herein.

As used herein in regard to smoking tobacco flavors, the terms "alter" and "modify" in their various forms mean "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired oriental, and Turkish tobacco-like notes on smoking and prior to smoking in the main stream and in the side stream are created or enhanced and may be readily controlled and maintained at the desired uniform level regardless of variations in the tobacco components of the blend.

Our invention further provides improved smoking tobacco additives and methods whereby various oriental and Turkish tobacco notes prior to smoking and on smoking are imparted (in the main stream and in the side stream) to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient at least one of the two tertiary pentamethylindanol derivatives of our invention prepared in accordance with the processes of our invention.

In addition to the one or both tertiary pentamethylindanol derivatives of our invention prepared in accordance with the processes of our invention, other flavoring and aroma additives may be added to the smoking tobacco materials or substitute therefor either separately or in admixture with one or both of the tertiary pentamethylindanol derivatives of our invention as follows:

(i) Synthetic Materials
Beta-ethyl-cinnamaldehyde;
Beta-cyclohomocitral;
Eugenol;
Dipentene;
β-Damascenone;
β-Damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;

2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[2,1b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils
Celery seed oil;
Coffee extract;
Bergamot Oil;
Cocoa extract;
Nutmeg oil; and
Origanum oil.

An aroma and flavoring concentrate containing one or both of the tertiary pentamethylindanol derivatives of our invention and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with the taste but insofar as the enhancement or the imparting of natural and/or oriental notes, we have found that satisfactory results are obtained if the proportion by weight of the sum total of one or both of the tertiary pentamethylindanol derivatives of our invention to smoking tobacco material is between 250 ppm and 1,500 ppm (0.025%–0.15%) of the active ingredients to the smoking tobacco material. We have further found that satisfactory results are obtained if the proportion by weight of the sum total of one or both of the tertiary pentamethylindanol derivatives of our invention is between 2,500 and 15,000 ppm (0.25%–1.50%).

Any convenient method for incorporating one or both of the tertiary pentamethylindanol derivatives prepared in accordance with the process of our invention in the tobacco product may be employed. Thus, one or both of the tertiary pentamethylindanol derivatives of our invention taken alone or along with other flavoring additives may be dissolved in a suitable solvent such as ethanol, pentane, diethyl ether and/or other organic solvents and the resulting solution may be either sprayed on the cured, cased and blended tobacco material or the tobacco material may be dipped into such solution. Under certain circumstances a solution containing one or both of the tertiary pentamethylindanol derivatives of our invention prepared in accordance with the process of our invention taken alone or taken further together with other flavoring additives as set forth above mey be applied by means of a suitable applicator such as a brush or roller on the paper or leaf wrapper for the smoking product, it may be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have one or both of the tertiary pentamethylindanol derivatives of our invention in excess of the amount or concentrations above indicated so that when blended with other tobaccos, the final product will have the percentage within the indicated range.

In accordance with one specific example of our invention, an aged, cured and shredded domestic Burley tobacco is sprayed with a 20% ethyl alcohol solution of a 50:50 mixture of the compounds having the structures:

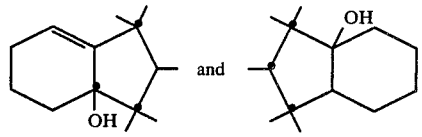

in an amount to provide a tobacco composition containing 800 ppm by weight of the mixture of compounds having the structures:

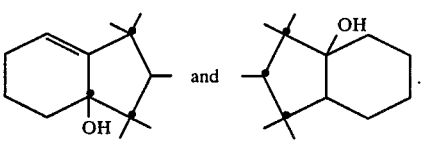

Thereafter, the alcohol is removed by evaporation and the tobacco is manufactured into cigarettes by the usual techniques. The cigarette, when treated as indicated, has a desired and pleasing aromas prior to smoking which can be described as oriental-like and Turkish and on smoking in the main stream and the side stream a sweet oriental-like and Turkish tobacco-like aroma with faint but aesthetically pleasing fruity and rum-like undertones.

While our invention is particularly useful in the manufacture of smoking tobacco such as cigarette tobacco, cigar tobacco and pipe tobacco, other smoking tobacco products formed from sheeted tobacco dust or fines may also be used. Likewise one or both of the tertiary pentamethylindanol derivatives of our invention can be incorporated with materials such as filter tip materials, seam paste, packaging materials and the like which are used along with tobacco to form a product adapted for smoking. Furthermore, one or both of the tertiary pentamethylindanol derivatives of our invention can be added to certain tobacco substitutes of natural or synthetic origin (e.g., dried lettuce leaves) and, accordingly, by the term "tobacco" is used throughout this specification is meant any composition intended for human consumption by smoking or otherwise, whether composed of tobacco plant parts or substitute materials or both.

The following Examples I, II, III and V illustrate methods of our invention used to manufacture the tertiary pentamethylindanol derivatives of our invention. Example IV sets forth a technique of the prior art. Examples following Example V serve to illustrate their organoleptic utilities of the tertiary pentamethylindanol derivatives of our invention.

All parts and percentages given herein are by weight unless otherwise specified.

EXAMPLE I

PREPARATION OF 5,6-DIHYDRO-1,1,2,3,3-PENTAMETHYL-3A(4H)-INDANOL

Reaction:

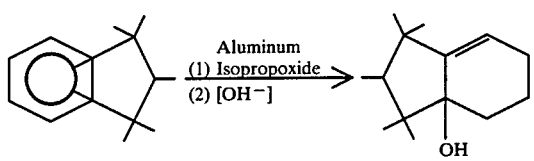

Into a 1-liter reaction vessel equipped with stirrer, thermometer, reflux condenser and heating mantle is placed the following materials:

| | |
|---|---|
| Tetrahydro pentamethylindane epoxide having the structure: | 160 grams |
| Aluminum isopropoxide | 160 grams |
| Anhydrous toluene | 400 ml |

The resulting reaction mass is heated to reflux and refluxed for a period of twenty four hours. At the end of the twenty four hour period, 600 ml water and 100 ml 50% sodium hydroxide is added to the reaction mass whereby the reaction mass now has a pH of between 10 and 12.

The reaction mass is poured into a separatory funnel and the organic layer is separated from the aqueous layer. The organic phase is washed twice with an equal volume of water and twice with an equal volume of saturated sodium chloride solution.

The crude material weighing 472.8 grams is dried and rushed over through a 2" splash column yielding the following fractions:

| Fraction No. | Vapor Temp. (°C.) | Liquid Temp. (°C.) | Vacuum mm/Hg. Pressure |
|---|---|---|---|
| 1 | 66/75 | 82/88 | 1.0 |
| 2 | 82 | 93 | 1.0 |
| 3 | 84 | 99 | 0.95 |
| 4 | 80 | 210 | 0.94 |

Fractions 2, 3 and 4 are bulked and redistilled on a 12" Goodloe column yielding the following fractions:

| Fraction No. | Vapor Temp. (°C.) | Liquid Temp. (°C.) | Vacuum mm/Hg. Pressure |
|---|---|---|---|
| 1 | 61 | 115 | 1.0 |
| 2 | 57 | 106 | 0.8 |
| 3 | 68 | 105 | 1.3 |
| 4 | 71 | 107 | 0.8 |
| 5 | 74 | 109 | 0.8 |
| 6 | 74 | 109 | 0.8 |
| 7 | 74 | 113 | 0.8 |
| 8 | 76 | 170 | 0.8 |
| 9 | 75 | 250 | 0.8 |

Figure 1:
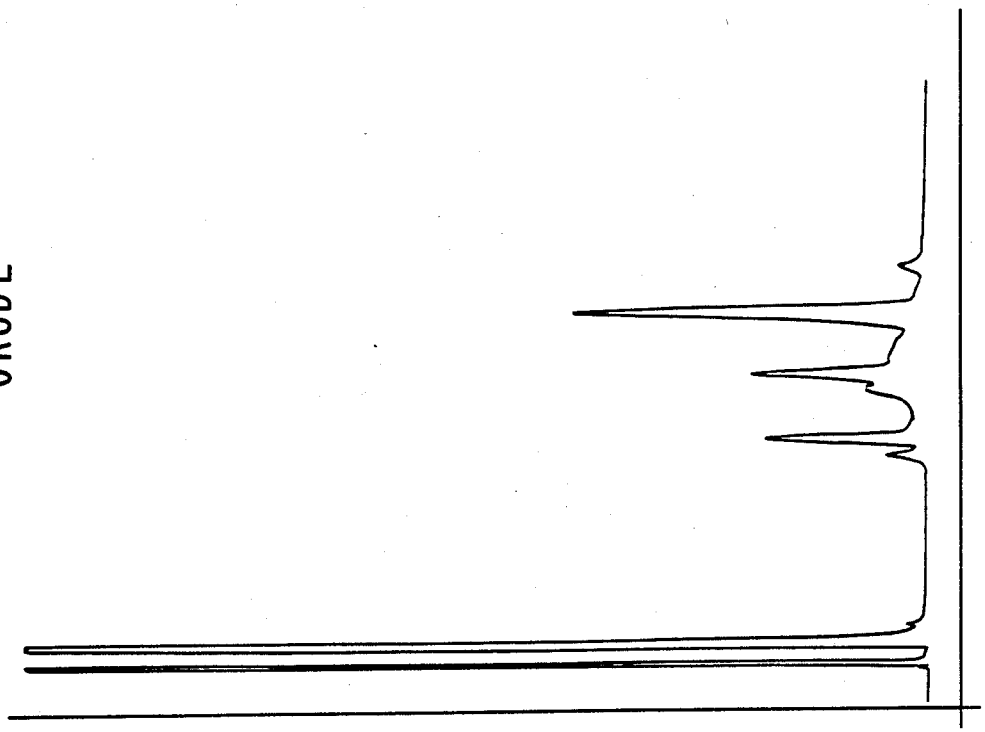
FIG. 1 is the GLC profile for the crude reaction product of Example I containing the compound defined according to the structure.

FIG. 1 is the GLC profile for the crude reaction product prior to distillation.

FIG. 2 is the GLC profile for Fraction 2 of the first distillation.

FIG. 3 is the GLC profile for Fraction 7 of the second distillation.

FIG. 4 is the GC-MS profile for the compound having the structure:

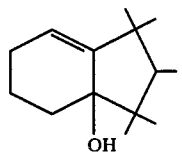

produced according to this example.

FIG. 5 is the NMR spectrum for Fraction 7 of the foregoing distillation which is for the compound having the structure:

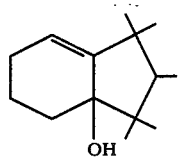

(conditions: Field strength: 100 MHz; Solvent: CFCl₃).

FIG. 6 is the infra-red spectrum for the compound having the structure:

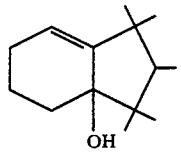

produced according to this example.

The resulting product having the structure:

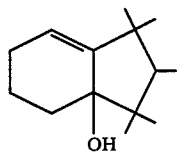

from a fragrance standpoint has a leafy, patchouli-like, vetiver-like and ginseng-like aroma with leafy, green, camphoraceous, woody, patchouli-like and musk undertones. From a flavor standpoint the compound having the structure:

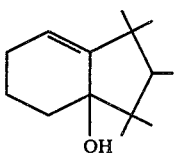

has a musky, patchouli-like and earthy aroma with a musky taste at 1.0 ppm causing it to be useful in walnut and blackberry flavored foodstuffs.

From a tobacco flavor point of view the compound having the structure:

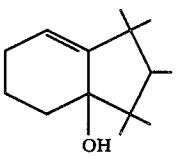

has a woody, oriental aroma and taste profile prior to and on smoking in the main stream and the side stream and gives rise to Turkish tobacco-like nuances in the main stream and the side stream on smoking.

EXAMPLE II

PREPARATION OF TETRAHYDRO-1,1,2,3,3-PENTAMETHYL-3A(4H)-INDANOL

Reaction:

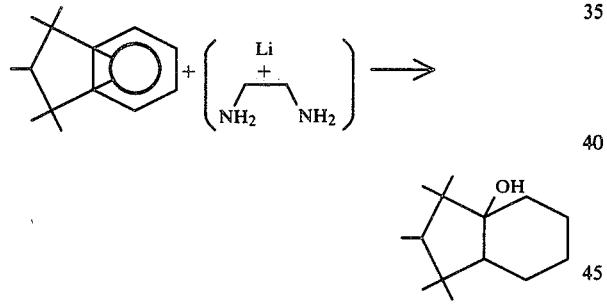

Into a 500 ml reaction flask equipped with reflux condenser, thermometer, heating mantle and stirrer is placed 250 ml of ethylene diamine. To the ethylene diamine, 52.0 grams (0.25 moles) of tetrahydro pentamethylindane epoxide having the structure:

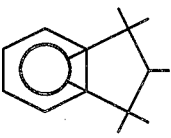

is added over a period of 10 minutes.

5.25 Grams of lithium wire is added to the reaction mass over a period of 10 minutes and the resulting mixture is heated, with stirring to 50° C. The reaction mass exotherms to 75°-80° C. and is cooled rapidly down to 50° C. The reaction mass is maintained, with stirring at 50° C. for a period of 1.5 hours. GLC sampling indicates completion of the reaction.

The reaction mass is quenched with 200 ml of water and extracted with 200 ml diethyl ether. The ether extract is dried over anhydrous sodium sulfate and stripped of solvent and then distilled to yield 40 grams of product, a compound defined according to the structure:

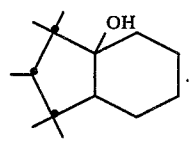

The distillation is carried out using a micro vigreux column yielding the following fractions:

| Fraction No. | Vapor Temp. (°C.) | Liquid Temp. (°C.) | Vacuum mm/Hg. Pressure | Weight of Fraction (gms.) |
|---|---|---|---|---|
| 1 | 50/65 | 86/92 | 1.8 | 0.8 |
| 2 | 87 | 96 | 1.8 | 1.0 |
| 3 | 90 | 103 | 1.8 | 14.0 |
| 4 | 90 | 120 | 1.8 | 16.0 |
| 5 | 90 | 180 | 1.8 | 16.0 |

FIG. 7 is the GLC profile for Fraction 5 of the foregoing distillation (Conditions: Carbowax column programmed at 100°-220° C. at 8° C. per minute).

FIG. 8 is the NMR spectrum for Fraction 5 of the foregoing distillation which is for the compound having the structure:

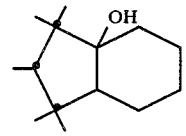

(conditions: Field strength: 100 MHz; Solvent: CFCl$_3$).

From a fragrance standpoint the resulting product has a patchouli-like, piney, rooty, woody and camphoraceous aroma profile with rooty, earthy, camphoraceous, woody and piney undertones. From a flavor standpoint the subject compound has a patchouli-like aroma and taste profile at 10 ppm causing it to be useful in walnut flavor foodstuffs.

From a tobacco flavor standpoint the resulting compound having the structure:

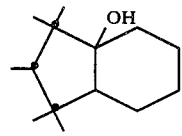

has a woody, oriental and Turkish tobacco-like aroma and taste profile both prior to and on smoking in the main stream and in the side stream.

EXAMPLE III

PREPARATION OF 5,6-DIHYDRO-1,1,2,3,3-PENTAMETHYL-3A(4H)-INDANOL

Reaction:

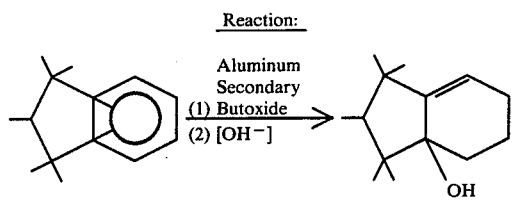

Into a 250 ml reaction flask equipped with stirrer, thermometer, reflux condenser and heating mantle are placed the following materials:

(i) 50.0 grams (0.24 moles) of tetrahydro pentamethylindane epoxide defined according to the structure:

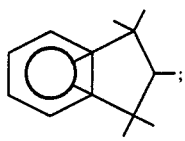

(ii) 29.56 grams (0.12 moles) of aluminum trisecondary butoxide defined according to the structure:

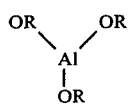

wherein R is secondary butyl; and (iii) 50 ml toluene.

The reaction mass is refluxed for a period of five hours during which time the reaction is followed by GLC. At the end of the five hour period, 100 ml of water is added to the reaction mass and the resulting mixture is then admixed with 50 ml of 50% aqueous sodium hydroxide whereby the resulting mixture has a pH of between 10 and 12.

The organic phase is separated from the aqueous phase and the organic phase is washed with one 100 ml portion of water, stripped of solvent and distilled yielding the following fractions:

| Fraction No. | Vapor Temp. (°C.) | Liquid Temp. (°C.) | Vacuum mm/Hg. Pressure |
|---|---|---|---|
| 1 | 65/70 | 80/82 | 3.5/3.0 |
| 2 | 70 | 90 | 3.0 |
| 3 | 80 | 95 | 3.0 |
| 4 | 91 | 117 | 2.3 |
| 5 | 90 | 160 | 2.3 |

FIG. 9 is the GLC profile for Fraction 3 of the foregoing distillation containing the compound having the structure:

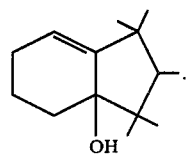

The resulting compound having the structure:

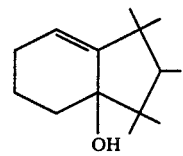

from a fragrance standpoint has a leafy, patchouli-like, vetiver-like and ginseng-like aroma profile with leafy, green, camphoraceous, woody, patchouli-like and musk undertones. From a flavor standpoint it has a musky, patchouli-like and earthy aroma with a musky taste at 1.0 ppm causing it to be useful in walnut and blackberry flavored foodstuffs. From a tobacco flavor point of view, the compound has a woody and oriental aroma and taste profile both prior to and on smoking in the main stream and the side stream.

EXAMPLE IV

PRIOR ART

PREPARATION OF 4,5,6,7-TETRAHYDRO-1,1,2,3,3-PENTAMETHYL-4-INDANOL

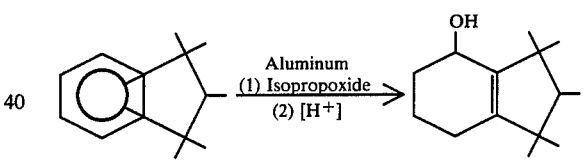

Into a 2-liter reaction vessel are placed 831 ml of toluene and 226.9 grams (1.11 moles) of aluminum isopropoxide. The mixture is heated to reflux and while refluxing, over a one hour period, tetrahydro pentamethylindane epoxide having the structure:

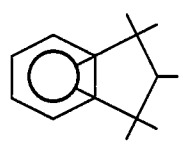

is added to the reaction mass. The reaction mass is continued to be refluxed for a period of twelve hours while being monitored by GLC analysis. An additional 0.5 moles of aluminum isopropoxide is added (101.5 grams) at the end of the twelve hour period and the refluxing is continued for an additional eight hours. At the end of the twenty hour period, an additional 50.7 grams of aluminum triisopropylate is added and the reaction mass is continued to be refluxed for an additional twenty two hours (total reflux time 42 hours).

The reaction mass is then washed with one 300 ml portion of aqueous 20% sulfuric acid followed by one 300 ml portion of water and then followed by one 300 ml portion of aqueous sodium bicarbonate (saturated). The organic layer is stripped of solvent and then distilled on a 12" stonepacked column yielding the following fractions:

| Fraction No. | Vapor Temp. (°C.) | Liquid Temp. (°C.) | Vacuum mm/Hg. Pressure |
|---|---|---|---|
| 1 | 45/74 | 109/101 | 8.5/7.0 |
| 2 | 68 | 107 | 7.0 |
| 3 | 79 | 111 | 7.0 |
| 4 | 90 | 115 | 7.0 |
| 5 | 90 | 125 | 7.0 |
| 6 | 47 | 235 | 7.0 |

Fractions 2–6 of this distillation product are bulked and redistilled on a spinning band column yielding the following fractions:

| Fraction No. | Vapor Temp. (°C.) | Liquid Temp. (°C.) | Vacuum mm/Hg. Pressure |
|---|---|---|---|
| 1 | 40/45 | 90/95 | 2.4/2.0 |
| 2 | 65 | 105 | 2.0 |
| 3 | 60 | 106 | 2.0 |
| 4 | 60 | 109 | 2.0 |
| 5 | 60 | 110 | 2.0 |
| 6 | 68 | 120 | 2.0 |
| 7 | 68 | 143 | 2.0 |
| 8 | 30 | 210 | 2.0 |

FIG. 10 is the GLC profile for Fraction 4 of the first distillation containing the compound having the structure:

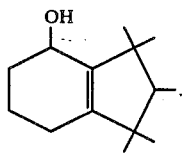

FIG. 11 is the GLC profile for Fraction 4 of the second distillation; the redistillation of bulked Fractions 2–6 of the first distillation containing the compound having the structure:

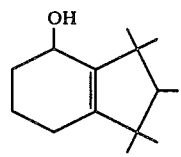

(conditions: Carbowax column programmed at 100°–220° C. at 8° C. per minute).

FIG. 12 is the NMR spectrum for Fraction 4 of the second distillation containing the compound having the structure:

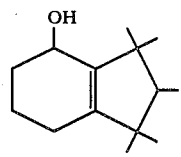

(conditions: Field strength: 100 MHz; Solvent: CFCl$_3$).

The resulting product also contains the compound having the structure:

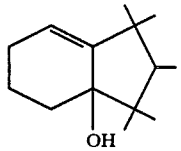

in an amount of approximately 50% by weight.

The resulting mixture containing the compound having the structure:

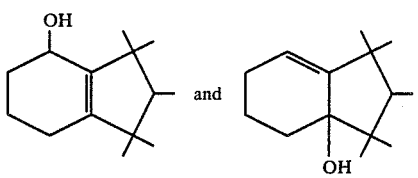

has a woody, balsamic aroma approximately one-third the intensity of the compound produced according to Examples I and III having the structure:

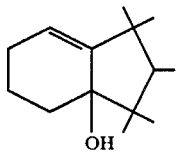

in the absence of the compound having the structure:

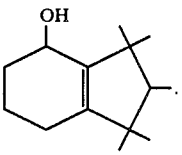

EXAMPLE V

PREPARATION OF TETRAHYDRO-1,1,2,3,3-PENTAMETHYL-3A(4H)-INDANOL

Reaction:

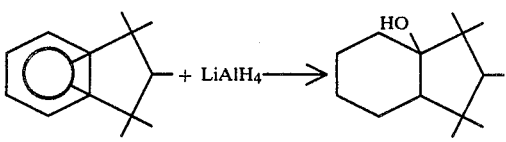

Into a 250 ml reaction vessel equipped with stirrer, thermometer and reflux condenser is placed a mixture of 11 grams (0.3 moles) of lithium aluminum hydride and 100 ml of diglyme. The resulting mixture is cooled with stirring to 0° C. Over a period of 30 minutes, 62.4 grams (0.3 moles) of tetrahydro pentamethylindane epoxide having the structure:

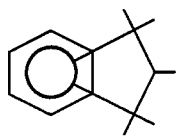

is slowly added to the resulting mixture.

The resulting mixture is heated to 174° C. (reflux temperature) and refluxed at 174° C. for a period of ten hours. GLC monitoring indicates completion of the reaction.

At the end of the ten hour period while maintaining the reaction mass at 0° C., the reaction mass is quenched with the following:

(i) 11 ml water;
(ii) 11 ml 15% sodium hydroxide; and
(iii) 33 ml water.

The organic phase is separated from the aqueous phase and the organic phase is filtered and distilled at 1 mm/Hg pressure (68% yield). This product has the structure:

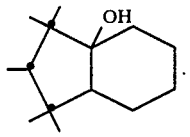

EXAMPLE VI

The following Chypre formulation is prepared:

| Ingredients | Parts by Weight |
| --- | --- |
| Musk ambrette | 40 |
| Musk ketone | 60 |
| Coumarin | 30 |
| Oil of bergamot | 150 |
| Oil of lemon | 100 |
| Methyl ionone | 50 |
| Hexyl cinnamic aldehyde | 100 |
| Hydroxycitronella | 100 |
| Oil of lavender | 50 |
| Texas cedarwood oil | 85 |
| Virginia cedarwood oil | 30 |
| Oil of sandalwood (East Indies) | 40 |
| Isoeugenol | 20 |
| Eugenol | 10 |
| Benzyl acetate | 30 |
| β-phenyl ethyl alcohol | 40 |
| a-phenyl ethyl alcohol | 30 |
| Oakmoss absolute | 30 |
| Vetiver oil Venezuela | 25 |
| Compound having the structure: | 25 |

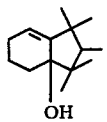

prepared according
to Example I or
Example III

The compound having the structure:

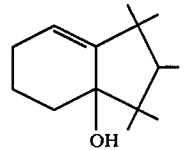

prepared according to Example I or III imparts to this Chypre formulation an intense patchouli-like, vetiver-like, leafy, ginseng aroma with leafy, green, camphoraceous, woody, patchouli and musk undertones. Accordingly, this formulation can be described as Chypre having leafy, patchouli-like, vetiver-like and ginseng nuances with leafy, green, camphoraceous, woody, patchouli and musk undertones.

EXAMPLE VII

PINE FRAGRANCE

The following pine fragrance formulation is produced:

| Ingredients | Parts by Weight |
| --- | --- |
| Isobornyl acetate | 100 |
| Camphor | 10 |
| Terpeineol | 25 |
| Fir balsam absolute (50% in diethyl phthalate) | 20 |
| Coumarin | 4 |
| Linalool | 30 |
| Fenchyl alcohol | 10 |
| Anethol | 12 |
| Lemon terpenes washed | 50 |
| Borneol | 5 |
| Galbanum oil | 5 |
| Turpentine Russian | 150 |
| Eucalyptol | 50 |
| 2,2,6-trimethyl-1-cyclohexene-1-carboxaldehyde | 12 |
| Maltol (1% in diethyl phthalate) | 5 |
| The compound having the structure: | 28 |

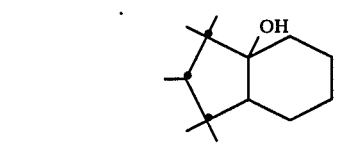

produced according
to Example II or V.

The compound having the structure:

prepared according to Examples II or V imparts to this pine fragrance an excellent patchouli-like, rooty, woody, camphoraceous, aroma nuance with rooty, earthy, camphoraceous and woody undertones. Accordingly, this formulation can be described as piney with rooty, patchouli-like, woody, camphoraceous nuances and rooty, earthy, camphoraceous and woody undertones.

EXAMPLE VIII

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 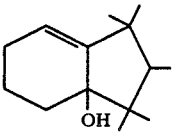 | A leafy, patchouli-like, vetiver-like and ginseng-like aroma with leafy, green, camphoraceous, woody, patchouli-like and musk undertones. |
| The compound having the structure: 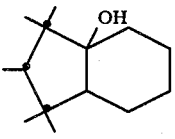 | A patchouli-like, piney, rooty, woody, camphoraceous aroma with rooty, earthy, camphoraceous, woody and piney undertones. |
| Perfume composition of Example VI | A leafy, patchouli-like, vetiver-like and ginseng nuances with leafy, green, camphoraceous, woody, patchouli and musk undertones. |
| Perfume composition of Example VII | A piney aroma with rooty, patchouli-like, woody, camphoraceous nuances and rooty, earthy, camphoraceous and woody undertones. |

EXAMPLE IX

PERFUMED LIQUID DETERGENTS

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example VIII are prepared containing 0.10%, 0.15%, 0.20%, 25%, 0.30% and 0.35% of the substance set forth in Table II of Example VIII. They are prepared by adding and homogeneously mixing the appropriate quantity of substance set forth in Table II of Example VIII below in the liquid detergent. The detergents all possess excellent aromas as set forth in Table II of Example VIII, the intensity increasing with greater concentrations of substance as set forth in Table II of Example VIII.

EXAMPLE X

PREPARATION OF COLOGNES AND HANDKERCHIEF PERFUMES

Compositions as set forth in Table II of Example VIII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VIII are imparted to the colognes and to the handkerchief perfumes at all levels indicated.

EXAMPLE XI

PREPARATION OF SOAP COMPOSITIONS

One hundred grams of soap chips [per sample] (IVORY ®, produced by the Procter & Gamble Company of Cincinnati, Ohio), are each mixed with one gram samples of substances as set forth in Table II of Example VIII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VIII.

EXAMPLE XII

PREPARATION OF SOLID DETERGENT COMPOSITIONS

Detergents are prepared using the following ingredients according to Example I of Canadian Pat. No. 1,007,948:

| Ingredient | Percent By Weight |
|---|---|
| "Neodol ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VIII. Each of the detergent samples has an excellent aroma as indicated in Table II of Example VIII.

EXAMPLE XIII

Utilizing the procedure of Example I at column 15 of U.S. Pat. No. 3,632,396, nonwoven cloth substrates useful as dry-added fabric softening articles of manufacture are prepared wherein the substrate, the substrate coating and the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20\text{-}22}$ HAPS
   22%—isopropyl alcohol
   20%—antistatic agent
   1%—of one of the substances as set forth in Table II of Example VIII.

Fabric softening compositions prepared according to Example I at column 15 of U.S. Pat. No. 3,632,396 having aroma characteristics as set forth in Table II of Example VIII, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example VIII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example VIII.

EXAMPLE XIV

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example VIII | 0.10 |

The perfuming substances as set forth in Table II of Example VIII add aroma characteristics as set forth in Table II of Example VIII which are rather intense and aesthetically pleasing to the users of the soft-feel, good-hold pump hair sprays.

EXAMPLE XV

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

Gafquat ®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled at 45° C. and 0.3 weight percent of perfuming substance as set forth in Table II of Example VIII is added to the mixture. The resulting mixture is cooled to 40° C. and blending is carried out for an additional one hour in each case. At the end of this blending period, the resulting material has a pleasant fragrance as indicated in Table II of Example VIII.

EXAMPLE XV

TOBACCO FORMULATIONS

Tobacco mixtures are prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. The cigarettes are divided into groups as follows:

Group A-treated with 500 ppm of the compound having the structure:

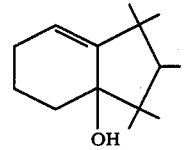

prepared according to either of Example I or Example III.

Group B-treated with 500 ppm of the compound having the structure:

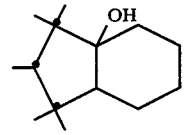

prepared according to Example II or Example V.

Group C-not treated with any compounds (control cigarettes).

The control cigarettes and the experimental cigarettes of Groups A and B, which contain the compounds defined according to the structures:

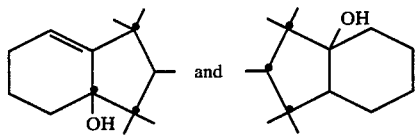

prepared according to Examples I, II, III and V, inclusive are evaluated by paired comparison and the results are as follows:

The experimental cigarettes of Groups A and B are found to have more body in tobacco smoke flavor and a fuller body sensation. The tobacco notes are described as "Turkish-like" with oriental nuances both prior to and on smoking in the main stream and the side stream. The flavor of the tobacco on smoking is, in addition, sweeter and more aromatic. All of the cigarettes are evaluated for smoke flavor with a 20 mm cellulose acetate flavor.

EXAMPLE XVII

FLAVOR FORMULATIONS

At the rate of 0.4 ppm a 50:50 mixture of the compound having the structure:

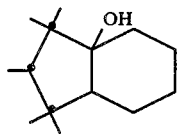

and the compound having the structure:

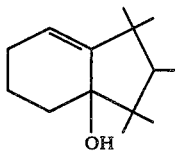

is added to a slurry containing water and 70% by weight of chopped shelled walnuts having an average particle diameter of 0.3 mm. The resulting slurry is then filtered and carefully dried at 45° F. in a forced air dryer. The resulting ground walnuts have a long-lasting, fresh walnut flavor even after remaining refrigerated in a standard refrigerator for a period of two weeks.

EXAMPLE XVIII

BLACKBERRY JAM

At the rate of 0.15 ppm, the compound having the structure:

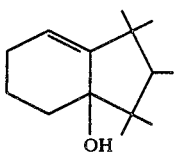

prepared according to Example I or III is added to SMUCKERS ® Blackberry Preserves. The resulting blackberry preserves retain their original fresh flavor after being removed from the vacuum jar in which it was originally marketed and the original blackberry flavor is retained for a period of six weeks when the resulting preserves are refrigerated in a standard kitchen refrigerator.

What is claimed is:

1. A process for augmenting or enhancing the aroma or taste of a walnut or blackberry flavored foodstuff or walnut or blackberry flavored chewing gum comprising the step of adding to said foodstuff or chewing gum from about 0.05 ppm up to about 150 ppm based on the total food composition or chewing gum composition of the compound having the structure:

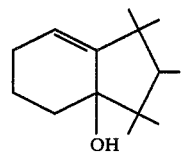

in the absence of the compound having the structure:

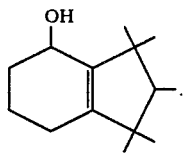

2. The process of claim 1 wherein there is additionally added to the foodstuff or chewing gum, the foodstuff or chewing gum being walnut flavored, the compound having the structure:

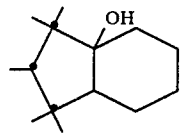

3. The process of claim 2 wherein the weight ratio of the compound having the structure:

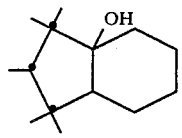

to the compound having the structure:

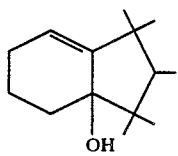

is a 50:50.

* * * * *